United States Patent
Uttenthal

(10) Patent No.: US 11,471,445 B2
(45) Date of Patent: Oct. 18, 2022

(54) COMPOSITIONS FOR THE PREVENTION AND TREATMENT OF ACUTE RENAL INJURY

(71) Applicant: AKI Therapeutics ApS, Hørsholm (DK)

(72) Inventor: Lars Otto Uttenthal, Madrid (ES)

(73) Assignee: AKI Therapeutics ApS, Hørsholm (DK)

( * ) Notice: Subject to any disclaimer, the term of this patent is extended or adjusted under 35 U.S.C. 154(b) by 439 days.

(21) Appl. No.: 16/624,858

(22) PCT Filed: Jun. 20, 2018

(86) PCT No.: PCT/EP2018/066390
§ 371 (c)(1),
(2) Date: Dec. 19, 2019

(87) PCT Pub. No.: WO2018/234372
PCT Pub. Date: Dec. 27, 2018

(65) Prior Publication Data
US 2021/0330649 A1    Oct. 28, 2021

(30) Foreign Application Priority Data

Jun. 23, 2017   (DK) .............................. PA201770488

(51) Int. Cl.
| | |
|---|---|
| *A61K 31/436* | (2006.01) |
| *A61K 47/61* | (2017.01) |
| *A61K 47/64* | (2017.01) |
| *A61K 9/00* | (2006.01) |
| *A61K 31/19* | (2006.01) |
| *A61K 31/215* | (2006.01) |
| *A61K 31/7048* | (2006.01) |
| *A61K 36/258* | (2006.01) |
| *A61K 38/13* | (2006.01) |

(52) U.S. Cl.
CPC .......... *A61K 31/436* (2013.01); *A61K 9/0019* (2013.01); *A61K 31/19* (2013.01); *A61K 31/215* (2013.01); *A61K 31/7048* (2013.01); *A61K 36/258* (2013.01); *A61K 38/13* (2013.01); *A61K 47/61* (2017.08); *A61K 47/64* (2017.08)

(58) Field of Classification Search
None
See application file for complete search history.

(56) References Cited

U.S. PATENT DOCUMENTS

| 2005/0261191 A1* | 11/2005 | Barasch .................... A61P 9/00 |
| | | 514/3.7 |
| 2008/0213370 A1 | 9/2008 | Desai et al. |
| 2012/0270791 A1 | 10/2012 | Leamon et al. |
| 2012/0308997 A1* | 12/2012 | Ruan .................. G01N 21/6456 |
| | | 435/7.9 |

FOREIGN PATENT DOCUMENTS

| CN | 1879889 A | * 12/2006 | .......... A61K 31/365 |
| JP | 2005-289913 A | 10/2005 | |
| JP | 2007-536260 A | 12/2007 | |
| KR | 10-1715294 B1 | 3/2017 | |
| RU | 2421209 C2 | 6/2011 | |
| WO | WO 00/45834 A2 | 8/2000 | |
| WO | WO 2005/107793 A2 | 11/2005 | |
| WO | WO 2007/065588 A1 | 6/2007 | |
| WO | WO 2015/084939 A1 | 6/2015 | |
| WO | WO 2015/108912 A1 | 7/2015 | |
| WO | WO 2016/153920 A1 | 9/2016 | |
| WO | WO 2017/100700 A2 | 6/2017 | |

OTHER PUBLICATIONS

Chou, N.K. et al., "Induction Immunosuppression With Basiliximab in Heart Transplantation" Transplantation Proceedings, 2008, pp. 2623-2625, vol. 40.
Park, Yeon-Hee et al., "Chemically conjugated novel liposomal formulation for intravenous delivery of cyclosporine A" Colloids and Surfaces A: Physicochem. Eng. Aspects, 2016, pp. 229-237, vol. 495.
Danish Patent and Trademark Office Action for PA 2017 70488 dated Feb. 1, 2018.
Database WPI, Week 200573, AN 2005-709062, XP002786511, Oct. 20, 2005.
Database WPI, Week 201726, AN 2017-201489, XP002786512, Mar. 10, 2017.
International Search Report for PCT/EP2018/066390 dated Dec. 10, 2018.
Partial Search Report for PCT/EP2018/066390.
Office Action for RU 2020102454 dated Oct. 21, 2021.
Search Report for RU 2020102454 dated Oct. 21, 2021.
Fu, Yu et al., "Renal-targeting triptolide-glucosamine conjugate exhibits lower toxicity and superior efficacy in attenuation of ischemia/reperfusion renal injury in rats" Acta Pharmacologica Sinica, 2016, pp. 1467-1480, vol. 37.
Yang, Chul Woo et al., "Pharmacological Preconditioning with Low-Dose Cyclosporine or FK506 Reduces Subsequent Ischemia/Reperfusion Injury in Rat Kidney" Transplantation, Dec. 2001, pp. 1753-1759, vol. 72, No. 11.
Zhou, Peng et al., "Kidney-targeted drug delivery systems" Acta Pharmaceutica Sinica. B, 2014, pp. 37-42, vol. 4, No. 1.
Office Action for JP 2020-520713 dated Jul. 4, 2022.

* cited by examiner

*Primary Examiner* — Dale R Miller
(74) *Attorney, Agent, or Firm* — Knobbe Martens Olson & Bear LLP

(57) ABSTRACT

Pharmaceutical compositions are provided for the treatment, pre-emptive treatment or prevention of acute renal injury.

7 Claims, No Drawings

COMPOSITIONS FOR THE PREVENTION AND TREATMENT OF ACUTE RENAL INJURY

CROSS REFERENCE TO RELATED APPLICATIONS

This application is a U.S. National Phase Application of PCT International Application Number PCT/EP2018/066390, filed on Jun. 20, 2018, designating the United States of America and published in the English language, which is an International Application of and claims the benefit of priority to Danish Patent Application No. PA201770488, filed on Jun. 23, 2017. The disclosures of the above-referenced applications are hereby expressly incorporated by reference in their entireties.

FIELD OF INVENTION

The present invention provides compositions comprising agents for the prophylaxis, pre-emptive treatment or treatment of acute renal injury (ARI). As such, it will be useful in the fields of medicine and surgery, especially in critical care medicine, and indeed in all medical fields in which serious diseases, accidents and therapeutic or diagnostic interventions put the patient at risk of ARI.

BACKGROUND OF INVENTION

Definition of Acute Renal Injury (ARI)

In the following, the term acute renal injury (ARI) refers to any acutely arising cellular damage within the kidney that is sufficient to cause a loss of one or more of several renal functions, whether or not the cellular damage is detectable by microscopy or the functional loss is detectable by a change in the concentration of a renal functional marker substance such as serum creatinine. Such renal injury may be detected by a rise in the circulating or urinary concentration of one or more of a number of renal injury markers that are released from cells within the kidney in response to a noxious process.

Classification of Causes of ARI

ARI may have many different causes; these are usually grouped under three different headings: 1) ischemia/reperfusion, 2) nephrotoxic, and 3) inflammatory. Some definitions of "nephrotoxic" widen the term to refer to any noxious influence on the kidney, so that it also covers ischemia/reperfusion and inflammatory injury. Here the term will be used to refer to toxic effects on the kidney exerted by substances that are not native to the body, especially to drugs.

Ischemia/reperfusion injury (IRI) refers to cell or organ injury resulting from a temporary cessation or drastic reduction of the arterial blood supply to the cell or organ, so that the cells are deprived of oxygen and the essential nutrients to maintain normal activity, this being followed by a restoration of the blood supply with consequent cellular responses to the temporary deprivation. Temporary anoxia or hypoxia will deprive the cells or organs of oxygen without depriving them of nutrients, and on reoxygenation, this results in hypoxia/reoxygenation injury (HRI), which has similarities to IRI. IRI in patients may result from surgical interventions, such as aortic clamping during cardiopulmonary bypass procedures, which temporarily deprives the kidneys and lower part of the body of arterial blood.

Nephrotoxic injury (NI) herein refers to injury to the kidney or certain of its constituent cells by agents that are not intrinsic to the healthy organism. Such agents are commonly drugs given with a therapeutic intent, such as aminoglycosides, certain other antibiotics, and cytotoxic agents given to treat cancers, but they may also be toxins unwittingly ingested with food, such as plant and fungal toxins or toxic agents, whether man-made or natural, that contaminate the environment.

Inflammatory injury (II) to the kidney is a broad term covering injuries that result from inflammatory mediators intrinsic to the body or extrinsic agents, such as bacterial antigens, that cause the release of inflammatory mediators, when they act on the kidney to provoke an inflammatory response which may be harmful to the kidney as a whole or to certain of its cells and structures. An example would be lipopolysaccharide(s) (LPS) from Gram-negative bacteria, which will provoke a deleterious inflammatory response in the kidney. As LPS is extrinsic, its action could in fact also be described as nephrotoxic.

In human disease, it is often impossible to classify ARI as being due to a single one of these causes. The most common cause of ARI in hospitalized patients is sepsis, and this may comprise both aspects of IRI and II. Sepsis may cause severe hypotension (septic shock), which may lead to hypoperfusion and failure of vital organs such as the kidneys. However, the injury due to prolonged hypoperfusion is not identical with IRI, but may be an intermediate state in which processes characteristic of both ischemia and reperfusion are going on in parallel. In addition, it has been questioned whether the kidney is in fact hypoperfused in sepsis, as physical measurements of renal blood flow have shown hyperemia. This has been countered with evidence that discrete parts of the intrarenal circulatory system may be hypoperfused, while the kidney as a whole is hyperemic. At the same time, a major causative role for ARI is sepsis, in which the renal injury has been attributed to II resulting from the systemic inflammatory response and the raised levels of circulating inflammatory mediators together with the presence of bacterial antigens such as LPS.

Intracellular Pathways Involved in ARI

Just as the causes of ARI in sepsis are poorly understood, the intracellular pathways through which the damage is mediated are by no means fully elucidated. The causes of ARI commonly result in the death of renal cells by either necrosis, apoptosis or necroptosis, seen especially in the renal tubular epithelial cells. Some cells are sublethally injured and can survive, while others are destined to die through one or other of the mentioned processes of cell death. Among the injurious factors that are regarded as significant are:

1) Mitochondrial permeability transition involving pore (mptp) formation. This may take place in response to NI or IRI, especially the reperfusion phase. The renal proximal convoluted tubule cells are metabolically highly active and are richly supplied with mitochondria. The formation of mptps is initiates cellular processes leading to both necrosis and apoptosis. The pores are formed in the inner mitochondrial membrane and increase mitochondrial permeability to molecules of up to 1500 Da in molecular mass. This leads to mitochondrial swelling which may rupture the outer mitochondrial membrane, leading to the release of cytochrome c into the cytoplasm and inevitable cell death. Mitochondrial permeability transition is modulated by members of the bcl-2 gene family and the mptp is regulated by the protein cyclophilin D (cypD), the action of which is blocked by the binding of the immunosuppressive antibiotics, the cyclosporins.

2) FAS/FAS-L pathway, downstream MAPK (mitogen-activated protein kinases) and JNK (c-Jun N-terminal kinase) signal transduction, or the RANK/RANK-L (receptor activator of NF-kB) pathway via activation of the caspase cascade. The caspase cascade resulting in apoptosis can be triggered either by cell-death receptors such as the tumor necrosis factor receptor 1 (TNF-R1) and Fas/CD95/APO1, or by the mitochondrial release of cytochrome c.

3) Activation of nuclear factor kappa B (NF-κB) occurs in the renal tubular epithelial cells by a redox-independent pathway which is sensitive to intracellular ionized calcium levels. Inducers of NF-κB activity include reactive oxygen species (ROS), TNFα, interleukin 1-beta (IL-1β) and LPS. NF-κB consists of a set of related transcription factors that play a central role in the inflammatory response. It upregulates a whole series of cytokines and chemokines that are involved in the recruitment of inflammatory cells around the injured kidney cells. A result of its actions and of the inflammatory cells that it recruits, the initial inflammatory response passes over to a process of fibrosis that may contribute to long-term impairment of kidney function.

Drugs that are Known to Ameliorate IRI, NI and II
Cyclosporins and Other Immunosuppressive Antibiotics Among the many drugs that have been found experimentally to ameliorate IRI in one or more tissues or organs are the cyclosporins. This is a series of cyclical polypeptide antibiotics which are commonly referred to as calcineurin inhibitors. Calcineurin is a calcium-dependent serine-threonine phosphatase which dephosphorylates and thus activates the transcription factor NFATc (nuclear factor of the activated T cell), which in turn upregulates the expression of interleukin 2 (IL-2) and stimulates the growth and differentiation of the T cells in response to non-self antigens. This pathway is blocked by the cyclosporins, which bind to cypD and inhibit calcineurin. The cyclosporins are hence used as immunosuppressive agents in organ transplantation, cyclosporin A being the most commonly employed. However, another consequence of cypD binding is to inhibit the opening of the mptps, which helps protect the cell from mitochondrially induced apoptosis and necrosis.

Cyclosporin A consists of 11 amino-acid residues and has a molecular mass of 1203. The cyclosporins form a large family of closely related drugs individually identified by the letters A to Z. Of particular interest are cyclosporin G, in which the L-α-amino-butyryl residue of cyclosporin A is replaced by L-norvaline, and SDZ IMM 125, also known as oxeclosporin, which is the 2-(O-(2-hydroxyethyl)-D-serine$^8$) analog of cyclosporine A. These two analogs are reported to show less nephrotoxic activity than cyclosporin A. The cyclosporins, exemplified by the index compound cyclosporin A, have long been known to protect cells from IRI, e.g. in the heart (Duchen et al 1993; Hausenloy et al 2012) and brain (Li et al 1997) and even in multiple organs following cardiac arrest (Cour et al 2014). Cyclosporin A has also been shown to protect mouse kidneys from NI (Wen et al 2012). However, for use in patients in which the commonest cause of ARI is sepsis, the use of agents of known immunosuppressive action raises the question of how the beneficial action on the injured kidney can be obtained without compromising the patient's cellular immune responses to the infection. Other immunosuppressive antibiotics such as tacrolimus, sirolimus (also known as rapamycin) and everolimus (the 40-O-(2-hydroxyethyl) derivative of sirolimus) have also been noted to have ameliorating effects on tissue ischemia.

The calcineurin inhibitors cyclosporin A and tacrolimus are themselves known to produce NI in a proportion of transplanted kidneys, especially those kidneys that have been subjected to a prolonged period of cold ischemia prior to transplantation. In some cases, the NI is acute, but more often the NI is seen after prolonged use of these immunosuppressants. The mechanism is not fully understood, but seems to involve arteriolar vasoconstriction and endothelial damage resulting in thrombotic microangiopathy, followed by longer-term interstitial fibrosis. Although this type of NI has not been studied in non-transplanted kidneys, the possibility of longer-term nephrotoxicity if the drugs are used to treat acute ARI due to other causes must be taken into account. This means that the drugs must be given for only a short period of time as early as possible after the onset of ARI. While sirolimus and everolimus, which are not calcineurin inhibitors, are associated with a much lower incidence of NI in the transplanted kidney, a few cases of thrombotic microangiopathy have also been observed when these are used for post-transplant immunosuppression. However, these cases are rare, and conversion to sirolimus prevents the progression of cyclosporin A nephrotoxicity (Sereno et al 2014).

Pentacyclic Triterpenoids

A different class of drugs which have been found to ameliorate both IRI and inflammation in various tissues and organs consists of pentacyclic triterpenoids of plant origin, such as celastrol and betulinic acid. The pentacyclic triterpenoids are a large group of compounds, the individual members of which may show a selection of biological activities including anti-inflammatory, anti-neoplastic, anti-diabetic and hormonal activities, some also being toxic to insects and fish and some being toxic to the liver and other organs in mammals.

Celastrol reduces infarct size and fibrosis in a rat model of acute myocardial infarction, possibly by triggering expression of the cardioprotective protein HO-1, while reducing myofibroblast and macrophage infiltration in the peri-infarct area (Der Sarkissian et al 2014). After ischemic stroke in a rat model, celastrol reduced neurological deficit and infarct sizes, and downregulated the expression of p-JNK, p-c-Jun and NF-κB (Li et al 2012). Celastrol also ameliorated renal IRI, preventing the upregulation of pro-inflammatory mediators by suppressing the nuclear translocation of NF-κB subunit p65 (Chu et al 2014). Pristimerin, the methyl ester of celastrol, has been noted to have similar anti-inflammatory effects to those of celastrol, but has not been tested in tissue damage models.

Betulinic acid pretreatment reduced the release of the myocardial damage marker enzymes LDH and CK, and reduced cardiomyocyte apoptosis in a rat model of myocardial IRI (Xia et al 2014). It also protected against cerebral ischemia-reperfusion injury in mice by reducing oxidative and nitrosative stress (Lu et al 2011). Betulinic acid pretreatment also protected against renal IRI by attenuating oxidant responses, improved microscopic damage and renal function, while inhibiting neutrophil infiltration (Eksioglu-Demiralp et al 2010).

Saponins and Flavonoids

A related class of plant-derived drugs consists of the saponins, which are amphipathic glycosides with detergent activity that are composed of one or more hydrophilic glycoside moieties combined with a lipophilic terpene derivative. Multifarious medicinal properties have also been ascribed to these drugs. Into this class falls the compounds hesperidin, a flavonoid present in the peel of citrus fruits, and its derivative diosmin, which is used to increase venous tone and reduce capillary permeability. The saponin β-escin has been used for the same purpose. These compounds reduce neutrophil adhesion to the vascular endothelium and hence the entry of neutrophils into inflamed tissue, thus exerting an anti-inflammatory effect. Anti-neoplastic and antioxidant (free radical scavenging) effects have been reported. Saponins extracted from *Panax quinquefolium* have also been demonstrated to have significant effects to ameliorate the consequences of IRI (see e.g. Li et al 2014).

Apart from its effects to reduce edema, diosmin pretreatment ameliorates the consequences of IRI in an ex vivo model of the rat heart (Senthamizhselvan et al 2014), cerebral IRI in a mouse model (Liu et al 2014) and hepatic IRI in rats (Tanrikulu et al 2013). Hesperidin has also been found to have protective effects on IRI in various organs. On the other hand, while β-escin also ameliorates the effects of focal cerebral ischemia, a suspicion that it might be associated with NI was aroused through its use in cardiopulmonary bypass surgery in children (Hellberg et al 1975).

SUMMARY OF THE INVENTION

In view of the above considerations, the invention therefore consists of pharmaceutical compositions comprising combinations and formulations of known drugs of the above-mentioned classes for the prophylaxis, pre-emptive treatment or treatment of acute renal injury (ARI) of ischemic, nephrotoxic or inflammatory origin, or combinations of these causative factors. In those cases where the drug is known to have an action that may be deleterious to the patient, such as immunosuppression in the presence of serious infection, it is a purpose of the invention to formulate or derivatize the drug so that it is targeted at the kidney or at least away from the immune cells whose functions should not be inhibited. It is a characteristic of the pentacyclic triterpenoids, saponins and flavonoids that have been tested individually for protective action in ARI that the effects have been partial. In consequence, it is also a purpose of the invention to combine drugs of these different classes that individually ameliorate the results of ARI through different pathways in order to obtain a synergic effect to prevent further damage after the onset of ARI. Accordingly, the pharmaceutical compositions comprise:

A composition comprising a drug chosen from a list comprising members of the cyclosporin family, including oxeclosporin, and the non-cyclosporin compounds tacrolimus, serolimus and everolimus, wherein the composition is formulated for intravenous administration in the form of a conjugate, or liposome, micelle or nanoparticle suspension hindering its uptake by lymphocytes and/or targeting the drug principally to the kidney, said composition being used for the prophylaxis and/or pre-emptive treatment and/or treatment of acute renal injury.

A composition comprising a combination of drugs formulated for intravenous administration, the combination consisting of a pentacyclic triterpenoid chosen from a list comprising celastrol, pristimerin and betulinic acid together with a saponin or flavonoid chosen from a list comprising diosmin, hesperidin and saponins from *Panax quinquefolium*.

In the following detailed description of the invention, specific combinations, formulations and derivatizations as well as uses of the composition will be described, together with details of the practical performance of the invention.

DETAILED DESCRIPTION OF THE INVENTION

Targeting the Immunosuppressive Antibiotics Towards the Kidney

The aforementioned immunosuppressive agents that can ameliorate tissue injury including ARI can be given in substantially unmodified form to patients that are free of significant infection. However, a substantial number of patients with ARI have severe infections in which immunosuppression would be regarded as dangerous. It is hence a purpose of the present invention to create derivatives or conjugates of these substances that will hinder their uptake by lymphocytes and favor their uptake by the kidney. By "conjugate" is meant a chemical compound in which the index substance is chemically linked by means of a covalent or dative/coordinate bond to another substance, which in this case enables the resulting conjugate to bind to a biological target molecule. If uptake of such a derivative or conjugate by the kidney leads to a many-fold greater drug concentration in that organ than systemic concentrations in general, an effective concentration in the kidney can be obtained at low dosage, while the general systemic concentration is inadequate to produce unwanted or adverse effects.

It is also a feature of said agents that they are very sparingly soluble in water (insoluble in layman's terms). However, they are soluble in lipids and cell membranes, so that they can be absorbed with a limited bioavailability when administered orally. In the seriously ill patients that are at high risk of ARI, oral administration may be impracticable, and the agents must be given intravenously. Formulations have long since been developed to permit intravenous administration in the form of the infusion of oil-in-water emulsions, given through micropore filters to prevent the administration of unacceptably large particles or droplets. The targeted derivatives or conjugates of these agents are to be administered intravenously in a similar manner.

A further feature that said agents have in common is that they lack reactive groups (amino, carboxyl, sulfhydryl or aromatic groups) that permit conjugation or derivatization by the simplest methods. It should be noted, however, that diosmin is a glycoside containing two hexose units. They do, however, all present a hydroxyl group that can be used for conjugation. In the case of oxeclosporin and everolimus, there is an additional hydroxyl group in the O-(2-hydroxyethyl) side chain.

To target these agents to the kidney, they are conjugated to carriers that are taken up by the megalin receptors (multi-ligand endocytic receptors highly expressed in the renal proximal tubules), which are often the structures that are most affected by ARI. The drug-carrier complex molecules must be capable of being filtered by the glomeruli so that they enter the tubular fluid to be taken up by the megalin receptors. This effectively limits the molecular size of the carriers to below a 30-kDa globular protein equivalent.

Three carriers are preferred among a considerable number of possible carriers:

1. Most preferred is neutrophil gelatinase-associated lipocalin (NGAL), preferably recombinant human NGAL. This is an endogenous protein of molecular weight 20.5 kDa for the non-glycosylated monomer protein chain of 178 amino-acid residues and approximately 25 kDa for the native glycosylated form. NGAL is particularly suitable as a targeting carrier because it is known to be taken up by the proximal convoluted tubular epithelial cells via the megalin receptors, apart from also being rapidly upregulated and secreted by these and other renal tubular cells in ARI and hence serving as an early diagnostic marker for ARI. It has also been suggested that NGAL itself may have a therapeutic effect in ARI, but this remains unsubstantiated. NGAL also binds to a more specific receptor known as 24p3R, which is found on renal tubular and certain other cells, but not on immunocompetent cells. The preferred form of recombinant human NGAL to be used is the non-glycosylated form, which may, for example, be obtained by expressing it in transformed *Escherichia coli* cells. A more preferred form of recombinant human NGAL is the modified form in which the cysteine residue in position 87 of the 178-amino-acid-residue chain length of the mature protein is absent, for example being replaced by a serine or other non-cysteine amino-acid residue. This will prevent the covalent self-association of the protein from forming dimers linked by a disulfide bridge.

2. A second possible carrier is the natural enzyme lysozyme, preferably recombinant human lysozyme. This is an endogenous protein of molecular weight 14 kDa.

3. A third possible carrier is low-degree N-acetylated hydroxyethyl low-molecular-weight chitosan. Chitosan is a natural copolymer of glucosamine and N-acetyl-glucosamine derived from chitin. It is specifically taken up by renal tubular cells and shows excellent biocompatibility and biodegradability. The hydroxyethyl chitosan is of molecular weight no greater than 20 kDa and is randomly N-acetylated to the 10% level. The drug moiety is linked via a succinic acid spacer arm. This technique has given excellent results for targeting the sparingly water-soluble steroid drug prednisolone to renal tubular cells, such that 13-fold higher renal prednisolone concentrations were obtained than with the unconjugated prednisolone controls (Yuan et al 2007, 2009, 2011).

Other low-molecular-weight protein carriers than the two mentioned above can be employed, including aprotinin, a 6-kDa protease inhibitor from bovine pancreas or lung. However. This is less preferred, as it is not a human protein, so that occasional allergic reactions have been seen, and it has been associated with an increased incidence of ARI when used at high dosage as an anti-fibrinolytic agent in cardiopulmonary bypass surgery.

Conjugation of the Drug to the Carrier

Because the only reactive group of the proposed immunosuppressive drugs is the hydroxyl group, conjugation is performed via this group. This type of conjugation must be carried out in the absence of water and alcohols. All the drugs are highly soluble in dimethyl sulfoxide (DMSO), so dry DMSO forms the medium for conjugation. The hydroxyl group is activated by one of the agents N,N'-carbonyldiimidazole (CDI), N,N'-disuccinimidyl carbonate (DSC), or N-hydroxysuccinimidyl chloroformate so that it can form a carbamate linkage with an amino group on the carrier. This and other suitable procedures are known to prior art (Yuan et al 2007, Hermanson 2013). After activation, the drugs can alternatively be linked to a moiety that confers further, more practicable conjugation possibilities, such 4-(aminomethyl) pyridine. This attaches a pyridine ring that can form the basis of conjugation via the platinum(II)-based Universal Linkage System (ULS; Kreatech Diagnostics, Amsterdam, The Netherlands). This platinum linker forms stable coordinative bonds with pyridyl groups or other types of aromatic nitrogens, and can be conjugated to thiol groups in proteinaceous carriers such as lysozyme (Dolman et al 2012).

Formulation of the Pentacyclic Triterpenoid/Saponin Combinations

Many of the considerations that apply to the immunosuppressive agents mentioned with respect to structural characteristics and their possibilities for conjugation also apply to the pentacyclic triterpenoids, flavonoids and saponins in the compositions of the present invention. They are sparingly soluble, conventionally regarded as insoluble, in water or buffers at near-neutral pH, and require special conditions, such as solution in strong alkali or organic solvents, to dissolve them. Diosmin, being a glycoside, is more water-soluble. Those that are in current human use are conventionally administered orally, often in micronized form to aid absorption and increase bioavailability. They are all readily soluble in DMSO, and can in principle be given as intravenous infusions of DMSO/water mixtures.

DMSO can in fact be administered to human patients in quite large doses and has an acceptable safety profile at low dosage. It has an intrinsic anti-inflammatory action and has been administered systemically for the treatment of rheumatoid arthritis, amyloidosis, raised intracranial pressure and interstitial cystitis. It has been applied topically as an analgesic and anti-inflammatory agent. The principal inconvenience that has been reported is a garlic-like halitosis. However, its beneficial effects have been weak and it has not reached general acceptance as an oral or intravenous medication.

Emulsions

Although it may be acceptable to permit a low percentage of DMSO in diluted solutions for intravenous infusion, the paradigm for a conventional intravenous formulation of the above-mentioned combinations would be the accepted formulations of other water-insoluble natural products, such praxitaxol or cyclosporin A involving emulsions with Cremophor EL (polyoxyethylated castor oil) and anhydrous ethanol mixtures that are diluted 5- to 20-fold in physiological saline before infusion. However, Cremophor EL has itself been associated with adverse reactions, including anaphylaxis, so alternative formulations based on pure triglyceride oils and lecithin can also be used.

Liposomes

An alternative way of delivering the aforesaid pentacyclic triterpenoids and saponins is in the form of aqueous suspensions of liposomes. For these hydrophobic drugs the liposomes are unilamellar and their production is well known to the skilled person. They can even be targeted to the kidney by embedding protein molecules with affinity for surface proteins of renal cells, e.g. antibodies against kidney cell surface antigens, in the hydrophilic outer membrane. However, the liposomes are unlikely to reach the apical surface of the renal tubular cells where the action of the contained drugs is believed to be most important. If they enter the glomerular filtrate through fenestrations in the glomerular endothelium, they will be most likely to target the mesangial cells. Therefore, use of liposomal preparations is seen more as an alternative to emulsions for the intravenous delivery of these drugs, as any targeting is unlikely to be optimal in the context of ARI.

Targeting of Pentacyclic Triterpenoids and Saponins to the Kidney

What is known of the toxicity profiles of the above-mentioned drugs is not such as to require the necessity of targeting them to the kidney to reduce systemic toxicity. However, targeting these drugs to the kidney will enable greater renal efficacy to be obtained at lower dosage and to diminish any systemic side effects that there may be. They can in fact be targeted to renal tubular cells by methods that are closely analogous to those described for the immunosuppressive drugs. A paradigm for the targeting of the triterpenoids and saponins is given by the targeting of triptolide. Triptolide is in fact a diterpenoid epoxide that is used in China to treat chronic renal diseases such as polycystic kidneys. As such, triptolide, its conjugate and their use to treat renal disease fall outside the scope of the present invention. It has both very low water solubility and toxic effects on the digestive, urogenital, circulatory and reproductive systems. Triptolide was conjugated to lysozyme by an ester linkage with a succinic acid spacer. The renal concentration of conjugate was 20-fold higher than that obtained with an equivalent dose of drug 30 min after intravenous injection (Zheng et al 2006). The triptolide-lysozyme conjugate showed only about one fifth of the hepatotoxicity shown by unconjugated triptolide and produced no adverse effects on the immune system. For the purpose of the present invention, the preferred targeting carrier to be used for conjugation is recombinant human NGAL, preferably in its non-glycosylated form and lacking a cysteine residue in position 87 of its protein chain.

In some embodiments, the compositions of the invention are for use in combination with other drugs.

In some embodiments, the composition, when used in combination with other drugs, is used for the prophylaxis and/or pre-emptive treatment and/or treatment of acute renal injury.

Embodiments According to the Invention

1. A composition comprising a drug chosen from a list comprising members of the cyclosporin family, including oxeclosporin, and the non-cyclosporin compound tacrolimus, serolimus and everolimus, wherein the composition is formulated for intravenous administration in the form of a conjugate, or liposome, micelle or nanoparticle suspension hindering its uptake by lymphocytes and/or targeting the drug principally to the kidney.

2. A composition comprising a combination of drugs formulated for intravenous administration, the combination consisting of a pentacyclic triterpenoid chosen from a list comprising celastrol, pristimerin and betulinic acid together with a saponin or flavonoid chosen from a list comprising diosmin, hesperidin and saponins from *Panax quinquefolium*.

3. A composition according to embodiments 1 or 2 for use in the prophylaxis and/or pre-emptive treatment and/or treatment of acute renal injury, wherein the composition is formulated for intravenous administration.

4. A composition according to embodiment 1, wherein the drug is cyclosporin A conjugated to human NGAL, which may optionally lack glycosylation and/or a cysteine residue in position 87 of its protein chain, or lysozyme, or a low-molecular-weight chitosan.

5. A composition according to embodiment 1, wherein the drug is cyclosporin G conjugated to human NGAL, which may optionally lack glycosylation and/or a cysteine residue in position 87 of its protein chain, or lysozyme, or a low-molecular-weight chitosan.

6. A composition according to embodiment 1, wherein the drug is oxeclosporin conjugated to human NGAL, which may optionally lack glycosylation and/or a cysteine residue in position 87 of its protein chain, or lysozyme, or a low-molecular-weight chitosan.

7. A composition according to embodiment 1, wherein the drug is tacrolimus conjugated to human NGAL, which may optionally lack glycosylation and/or a cysteine residue in position 87 of its protein chain, or lysozyme, or a low-molecular-weight chitosan.

8. A composition according to embodiment 1, wherein the drug is serolimus conjugated to human NGAL, which may optionally lack glycosylation and/or a cysteine residue in position 87 of its protein chain, or lysozyme, or a low-molecular-weight chitosan.

9. A composition according to embodiment 1, wherein the drug is everolimus conjugated to human NGAL, which may optionally lack glycosylation and/or a cysteine residue in position 87 of its protein chain, or lysozyme, or a low-molecular-weight chitosan.

10. The composition according to any one of embodiments 4 to 9, wherein the NGAL is in the form of any one of NGAL that lacks glycosylation, or NGAL that lacks the cysteine residue in position 87, or NGAL that lacks glycosylation and lacks the cysteine residue in position 87.

11. A composition according to embodiment 2, in which the combination of drugs comprises betulinic acid and diosmin.

12. A composition according to embodiment 2, in which the combination of drugs comprises celastrol and diosmin.

13. A composition according to embodiments 11 or 12, in which the drugs are conjugated to human NGAL, which may optionally lack glycosylation and/or a cysteine residue in position 87 of its protein chain, or lysozyme, or a low-molecular-weight chitosan.

14. The composition according to any one of embodiments 1-13 for use in the prophylaxis and/or pre-emptive treatment and/or treatment of acute renal injury, wherein the composition is combined with another drug.

15. The composition according to any one of embodiments 1-2, 4-13 for use in the prophylaxis and/or pre-emptive treatment and/or treatment of acute renal injury, wherein the composition is formulated for intravenous administration.

16. A method for prophylaxis and/or pre-emptive treatment and/or treatment of acute renal injury, comprising intravenous administration of the composition as defined in one of embodiments 1-2 and 4-13 to a subject in need of such prophylaxis and/or treatment.

Preferred Compositions of the Invention

The compositions of the invention comprise a compound chosen from members of the cyclosporin family, including oxeclosporin, and the non-cyclosporin compounds tacrolimus, serolimus and everolimus to be used preferably singly for the early treatment, pre-emptive treatment or prophylaxis of ARI. The compound is formulated in such a way that it can be given intravenously in the form of a conjugate, or liposome, micelle or nanoparticle suspension, the purpose of which is to hinder its uptake by lymphocytes and/or to target the drug principally to the kidney. A preferred compound is cyclosporin A, more preferred is cyclosporin G, and most preferred is oxeclosporin. Notwithstanding the preference for the use of a single compound, the compound may be combined or used together with other compounds that are shown to have an additive or synergistic beneficial effect on the treatment of ARI. A preferred carrier or conjugation partner to hinder the uptake of the compound by lymphocytes and/or to target the drug principally to the kidney is NGAL.

The compositions of the invention also comprise a combination of drugs consisting of a pentacyclic triterpenoid chosen from a list comprising celastrol, pristimerin and betulinic acid, with a saponin or flavonoid chosen from a list comprising diosmin, hesperidin and saponins from *Panax quinquefolium*. The drugs of the combination are formulated in such a way that the combination can be given intravenously. The drugs of the combinations can also be formulated as conjugates to target them principally to the kidney. A preferred combination is betulinic acid combined with diosmin, while a more preferred combination is celastrol combined with diosmin. A preferred carrier or conjugation partner is NGAL.

Indications for Use

The indications for the use of the compositions according to the present invention are:

1) Early treatment of ARI as soon as the clinician regards the diagnosis as being established by the clinical features and by objective markers such as a fall in urine output or a rise in urinary concentrations of one or more renal damage marker proteins such as NGAL, interleukin 18 (IL-18), liver fatty acid binding protein (L-FABP). kidney injury molecule 1 (KIM-1), insulin-like growth factor-binding protein 7 (IGFBP7), tissue inhibitor of metalloproteinases-2 (TIMP-2), monocyte chemo-attractant protein 1 (MCP-1), heat shock protein 70 (Hsp70), cysteine-rich protein 61 (Cyr61), osteopontin, dipeptidylpeptidase IV (DP4), cystatin C (cysC) and netrin-1, to name but those that have received most attention. Of these, only NGAL shows a response in plasma concentrations that can be reliably diagnostic of ARI. The rise is concentration of any one of these proteins must exceed a threshold level above which the clinician considers the response to be diagnostic.

2) Pre-emptive treatment of ARI when the clinician finds that the risk of ARI is high and there is a substantial, if not diagnostic, increase in the concentration of a renal damage marker protein.

3) Prophylaxis of ARI when the patient has suffered an event or has undergone a medical or surgical procedure (such as cardiopulmonary bypass surgery) which is known to be associated with a high risk of ARI.

Formulations

The principal aspects of the formulation of the compositions of the present invention, as delivered to the end user, have been described above. They are delivered as solutions, emulsions, or liposome preparations for dilution before being administered by intravenous infusion. A variety of aqueous diluents may be used, including, but not limited to, 0.9% sodium chloride solution, 5% dextrose solution, buffered saline, physiologically compatible buffers and the like. The compositions are typically given as dilutions of 1 in 5 to 1 in 20 by volume in the aqueous diluent.

The compositions may contain pharmaceutically acceptable auxiliary substances or adjuvants, including, without limitation, pH-adjusting and buffering agents and/or tonicity adjusting agents, such as, for example, succinic acid, citric acid, sodium acetate, sodium bicarbonate, sodium lactate, sodium hydroxide, sodium chloride, potassium chloride, calcium chloride, etc.

The pH value of the compositions and formulations according to the present invention may be adjusted to a pH of between 3 and 10; such as between 4 and 9; such as between 4 and 8; such as between 5 and 8; such as between 6 and 8; preferably between 6.5 and 7.5 such as wherein said composition has a pH of about 7, such as 7.4.

Administration

The compositions of the present invention are for intravenous administration by infusion of the diluted preparation. The timing of the administration is important. Administration should be carried out as soon as the attending clinician considers that an indication for use is present.

Preparations containing conjugates of the immunosuppressive antibiotics are typically given as a single dose, which may be repeated once after 24 hours. This is because the beneficial action on ARI is immediate, while prolonged use of the unconjugated active substances is associated with a slight, variable risk of provoking kidney damage of a different type, as previously described.

Preparations containing a pentacyclic triterpenoid/saponin combination are typically given as a single daily dose over a period of up to 5 days. If the ARI does not respond to treatment within this period, it is unlikely that any benefit will be obtained by prolonging the treatment.

Dosage

The dosage of the compositions of the present invention refer to the amount of each active substance administered in a single dose. When targeted conjugates are used, the dosage refers to the amount of active substance present in the conjugate.

For the targeted conjugates, the dosage may be no greater than one fifth or less, such as one tenth of one twentieth, of the conventional dose of the unconjugated drug substance. The dosages are therefore in the following ranges:

Conjugated cyclosporin A: 0.25 mg/kg to 1 mg/kg
Conjugated cyclosporin G: 0.25 mg/kg to 1 mg/kg
Conjugated oxeclosporin: 0.5 mg/kg to 2 mg/kg
Conjugated tacrolimus: 0.005 mg/kg to 0.02 mg/kg
Conjugated sirolimus: 0.5 microgram/kg to 2 microgram/kg
Conjugated everolimus: 0.5 microgram/kg to 2 microgram/kg
Celastrol: 0.5 mg/kg to 2 mg/kg (one tenth of this dose for a targeted conjugate)
Pristimerin: 0.5 mg/kg to 2 mg/kg (one tenth of this dose for a targeted conjugate)
Betulinic acid: 0.25 mg/kg to 1 mg/kg (one tenth of this dose for a targeted conjugate)
Diosmin: 0.5 mg/kg to 2 mg/kg (one tenth of this dose for a targeted conjugate)
Hesperidin: 0.5 mg/kg to 2 mg/kg (one tenth of this dose for a targeted conjugate)
*Panax quinquefolium* saponin: 0.5 mg/kg to 2 mg/kg (one tenth of this dose for a targeted conjugate)

EXAMPLES

The practice of the invention on animal models of ARI is illustrated by the non-limiting examples described below.

Animal models: There are many animal models of ARI in current use. The most commonly used are rodent models such as mice and rats. Non-limiting examples of models used are:

Ischemia/reperfusion injury: Sprague-Dawley or Wistar rats are most commonly used, but mice can also be employed. Non-limiting examples of a protocol for rats as well as one for mice are given by Mishra et al (2003).

Nephrotoxic injury: Both mice and rats are commonly used. A protocol in which ARI is induced in CD-1 mice by the intraperitoneal injection of folic acid is given by Wen et al (2012), while Mishra et al (2003) provide a protocol for the induction of ARI in mice by the intraperitoneal injection of cisplatin.

Inflammatory injury: Models of inflammatory ARI in rodents include the injection of high doses of LPS, the injection of bacteria, or cecal ligation and puncture to induce fecal peritonitis. Such models, and alternative models in non-rodent animals, have been discussed by Zarjou & Agarwal (2011) and Rabb et al (2016)

Administration of the compounds: Common to the compounds of the invention is that they are water-insoluble (except diosmin), planar molecules with few or no specific reactive groups, which interact with intracellular proteins to produce effects that may alleviate the consequences of ARI. When given orally, they are poorly absorbed and show a low bioavailability, in the region of 10-20%. In critically ill patients liable ARI, it will be necessary to give such drugs intravenously. Thus, intravenous administration is the preferred procedure for testing in experimental animals to ensure transferability to possible human use. The compounds are therefore formulated to permit intravenous administration. Intraperitoneal administration may be used as an alternative, which is, however, less comparable to the anticipated route of administration in patients.

Example 1

Testing of Compounds without Targeting to the Kidney

Celastrol, betulinic acid and diosmin are purchased from Sigma-Aldrich Co. Celastrol and betulinic acid are dissolved in DMSO and the solution diluted in 0.9% sodium chloride to give a concentration of at least 1 mg/mL of each active compound for intravenous, or alternatively, intraperitoneal injection. These compounds are tested alone and in combination for the prevention and/or treatment of ARI induced in mice by the intraperitoneal injection of folic acid, as described by Wen et al (2012). Doses of celastrol or betulinic acid are in the range of 5-50 mg/kg and those of diosmin in the range of 10-100 mg/kg. These are given intravenously into the tail vein. For testing the prevention of ARI, the compounds are given 30 minutes before the folic acid dose; for testing the treatment of ARI, the compounds are given 30 minutes after the folic acid dose. Dosage is repeated daily for 5 days. Urine is collected in metabolic cages and blood samples are from the saphenous vein on days 2, 3, 7 and 14. At least urea, creatinine and NGAL are measured in the samples. Groups of 12 mice each comprise normal controls, an untreated folic acid group, and three treatment groups with different doses or drug combinations.

Example 2

Confirmatory Testing of Compounds without Targeting to the Kidney

Confirmatory testing of the above compounds can be carried out in a rat model of ischemia-reperfusion injury (as described for example in Mishra et al, 2003). Doses of drugs are as determined in the light of the results obtained in Example 1, and must be given intravenously no earlier than the initiation of reperfusion for confirmation of treatment effect. Sampling will take place at time points during the first 24 hours and the same biomarkers will be measured.

Example 3

Testing of a Conjugated Compound Targeted to the Kidneys

The compound tested is any one of the conjugated compounds listed in the section on Dosage above and is tested at the corresponding dose range given in that section. The carrier or conjugation partner is non-glycosylated recombinant NGAL of the animal species in which the conjugate is tested. The protocols for testing are those given in Examples 1 and 2 above.

REFERENCES

Chu C, He W, Kuang Y et al (2014) Celastrol protects kidney against ischemia-reperfusion-induced injury in rats. J Surg Res 186:398-407.
Cour M, Abrial M, Jahandiez V, et al (2014) Ubiquitous protective effects of cyclosporine A in preventing cardiac arrest-induced multiple organ failure. J Appl Physiol 1985 117:930-936.
Der Sarkissian S, Cailhier J F, Borie M et al (2014) Celastrol protects ischaemic myocardium through a heat shock response with upregulation of haeme oxygenase-1. Br J Pharmacol 171:5265-5279.
Dolman M E, Harmsen S, Pieters E H (2012) Targeting of a platinum-bound sunitinib analog to renal proximal tubular cells. Int J Nanomedicine 7:417-433.
Duchen M R, McGuinness O, Brown L A et al (1993) On the involvement of a cyclosporin A sensitive mitochondrial pore in myocardial reperfusion injury. Cardiovasc Res 27:1790-1794.
Eksioglu-Demiralp E, Kardaş E R, Ozgül S et al (2010) Betulinic acid protects against ischemia/reperfusion-induced renal damage and inhibits leukocyte apoptosis. Phytother Res 24:325-332.
Hausenloy D J, Boston-Griffiths E A, Yellon D M (2012) Cyclosporin A and cardioprotection: from investigative tool to therapeutic agent. Br J Pharmacol 165:1235-1245.
Hellberg K, Ruschewski W, de Vivie R (1975) [Drug induced acute renal failure after heart surgery (author's transl., article in German). Thoraxchir Vask Chir 23:396-399.
Hermanson G T (2013) Bioconjugate techniques. 3rd edition, Academic Press, p. 249.
Li D, Liu M, Tao T Q, et al (2014) *Panax quinquefolium* saponin attenuates cardiomyocyte apoptosis and opening of the mitochondrial permeability transition pore in a rat model of ischemia/reperfusion. Cell Physiol Biochem 34:1413-1426.
Li P A, Uchino H, Elmer E, et al (1997) Amelioration by cyclosporin A of brain damage following 5 or 10 min of ischemia in rats subjected to preischemic hyperglycemia. Brain Res 753:133-140.
Li Y, He D, Zhang X, et al (2012) Protective effect of celastrol in rat cerebral ischemia model: down-regulating p-JNK, p-c-Jun and NF-κB. Brain Res 1464:8-13.
Liu X, Zhang X, Zhang J et al (2014) Diosmin protects against cerebral ischemia/reperfusion injury through activating JAK2/STAT3 signal pathway in mice. Neuroscience 268:318-327.
Lu Q, Xia N, Xu H et al (2011) Betulinic acid protects against cerebral ischemia-reperfusion injury in mice by reducing oxidative and nitrosative stress. Nitric Oxide 24:132-138.
Mishra J, Ma Q, Prada A et al (2003) Identification of neutrophil gelatinase-associated lipocalin as a novel early urinary biomarker for ischemic renal injury. J Am Soc Nephrol 14:2534-2543.
Rabb H, Griffin M D, McKay D B et al (2016) Inflammation in AKI: Current understanding, key questions, and knowledge gaps. J Am Soc Nephrol 27:371-379.
Senthamizhselvan O, Manivannan J, Silambarasan T et al (2014) Diosmin pretreatment improves cardiac function and suppresses oxidative stress in rat heart after ischemia/reperfusion. Eur J Pharmacol 736:131-137.
Sereno J, Nunes S, Rodrigues-Santos P et al (2014) Conversion to sirolimus ameliorates cyclosporine-induced nephropathy in the rat: focus on serum, urine, gene, and protein renal expression biomarkers. Biomed Res Int 2014:576929.
Tanrikulu Y, Sahin M, Kismet K et al (2013) The protective effect of diosmin on hepatic ischemia reperfusion injury: an experimental study. Bosn J Basic Med Sci 13:218-224.
Wen X, Peng Z, Li Y et al (2012) One dose of cyclosporine A is protective at initiation of folic acid-induced acute kidney injury in mice. Nephrol Dial Transplant 27:3100-3109.

Xia A, Xue Z, Li Y et al (2014) Cardioprotective effect of betulinic acid on myocardial ischemia reperfusion injury in rats. Evid Based Complement Alternat Med 2014: 573745.

Yuan Z X, Sun X, Gong T et al (2007) Randomly 50% N-acetylated low molecular weight chitosan as a novel renal targeting carrier. J Drug Target 15:269-278.

Yuan Z X, Zhang Z R, Zhu D et al (2009) Specific renal uptake of randomly 50% N-acetylated low molecular weight chitosan. Mol Pharm 6:305-314.

Yuan Z X, Li J J, Zhu D et al (2011) Enhanced accumulation of low-molecular-weight chitosan in kidneys: a study on the influence of N-acetylation of chitosan on the renal targeting. J Drug Target 19:540-551.

Zarjou A, Agarwal A (2011) Sepsis and acute kidney injury. J Am Soc Nephrol 22:999-1006.

Zheng Q, Gong T, Sun X et al (2006) Synthesis, characterization and in vitro evaluation of triptolide-lysozyme conjugate for renal targeting delivery of triptolide. Arch Pharm Res 29:1164-1170.

The invention claimed is:

1. A composition comprising a drug chosen from a cyclosporin, tacrolimus, serolimus or everolimus, wherein said drug is conjugated to a neutrophil gelatinase-associated lipocalin (NGAL) and wherein the conjugate is formulated for intravenous administration to a human subject.

2. The composition according to claim 1, wherein the drug is cyclosporin A conjugated to recombinantly produced human NGAL, which may optionally lack glycosylation and/or a cysteine residue in position 87 of its protein chain.

3. The composition according to claim 1, wherein the drug is cyclosporin G conjugated to recombinantly produced human NGAL, which may optionally lack glycosylation and/or a cysteine residue in position 87 of its protein chain.

4. The composition according to claim 1, wherein the drug is oxeclosporin conjugated to recombinantly produced human NGAL, which may optionally lack glycosylation and/or a cysteine residue in position 87 of its protein chain.

5. The composition according to claim 1, wherein the drug is chosen from tacrolimus, serolimus or everolimus and said drug is conjugated to recombinantly produced human NGAL, which may optionally lack glycosylation and/or a cysteine residue in position 87 of its protein chain.

6. The composition according to claim 1, wherein the NGAL is in the form of any one of NGAL that lacks glycosylation, or NGAL that lacks the cysteine residue in position 87, or NGAL that lacks glycosylation and lacks the cysteine residue in position 87.

7. A method for inhibiting acute renal injury, comprising administering the composition as defined in claim 1 to a subject in need thereof.

* * * * *

UNITED STATES PATENT AND TRADEMARK OFFICE
CERTIFICATE OF CORRECTION

PATENT NO. : 11,471,445 B2
APPLICATION NO. : 16/624858
DATED : October 18, 2022
INVENTOR(S) : Lars Otto Uttenthal It is certified that error appears in the above-identified patent and that said Letters Patent is hereby corrected as shown below:

In the Specification

In Column 5, Line 43, delete "serolimus" and insert --sirolimus--.

In Column 9, Line 25, delete "serolimus" and insert --sirolimus--.

In Column 9, Line 64, delete "serolimus" and insert --sirolimus--.

In Column 10, Line 16, delete "embodiments" and insert --embodiment--.

In Column 10, Line 39, delete "serolimus" and insert --sirolimus--.

In Column 11, Line 9, delete "(L-FABP)." and insert --(L-FABP),--.

In Column 11, Line 14, delete "(DP4)," and insert --(DPP4),--.

In Column 12, Line 58, after "(2016)" insert --.--.

In the Claims

In Column 15, Claim 1, Line 23 (Approx.), delete "serolimus" and insert --sirolimus--.

In Column 16, Claim 5, Line 14, delete "serolimus" and insert --sirolimus--.

Signed and Sealed this
Eighteenth Day of April, 2023

Katherine Kelly Vidal
*Director of the United States Patent and Trademark Office*